(12) United States Patent
Gramnäs

(10) Patent No.: US 6,808,540 B1
(45) Date of Patent: Oct. 26, 2004

(54) DEVICE AT A KNEE JOINT PROSTHESIS

(75) Inventor: Finn Gramnäs, Kinna (SE)

(73) Assignee: Gramtec Innovation AB, Kinna (SE)

( * ) Notice: Subject to any disclaimer, the term of this patent is extended or adjusted under 35 U.S.C. 154(b) by 0 days.

(21) Appl. No.: 10/130,642

(22) PCT Filed: Nov. 23, 2000

(86) PCT No.: PCT/SE00/02322

§ 371 (c)(1),
(2), (4) Date: May 20, 2002

(87) PCT Pub. No.: WO01/37763

PCT Pub. Date: May 31, 2001

(30) Foreign Application Priority Data

Nov. 23, 1999 (SE) ............................................ 99042244

(51) Int. Cl.[7] ................. A61F 2/64; A61F 2/68
(52) U.S. Cl. ........................................................ 623/44
(58) Field of Search ........................ 623/44, 39, 43, 623/45, 46

(56) References Cited

U.S. PATENT DOCUMENTS

| 4,145,766 A | | 3/1979 | May |
| 5,201,776 A | | 4/1993 | Freeman |
| 5,545,232 A | | 8/1996 | Van de Veen |
| 5,728,173 A | | 3/1998 | Chen |
| 5,800,566 A | * | 9/1998 | Gramnas ..................... 623/39 |
| 5,888,236 A | | 3/1999 | Van De Veen |
| 5,921,358 A | * | 7/1999 | Gramnas ................. 188/292.4 |

FOREIGN PATENT DOCUMENTS

| FR | 2677540 A1 | 12/1992 |
| SU | 1109153 A | 8/1984 |

* cited by examiner

Primary Examiner—Bruce E Snow
(74) Attorney, Agent, or Firm—Gardner Carton & Douglas (57) ABSTRACT

A device of the kind that comprises a polycentric link mechanism with at least four elements, namely one front and one back base element (10, 11) and one upper and one lower connecting element (12, 13). The upper connecting element (12) forms a unit fixedly attached to a thighbone part (21) of prosthesis and the lower connecting element (13) forms a unit fixedly attached to the shank part (22) of prothesis. The back base element (11) is pivotably connected at its upper end to the upper connecting element (12) and pivotably connected at its lower end to the lower connecting element (13) via a jointed attachment element (23), the movement of which is limited by a resilient stop device (29), whereby also the forward movement of the back base element (11) is limited when the knee joint is in a substantially straight position. The attachment element (23) shows a cam curve (26) or the like arranged to cooperate with the resilient stop device (29) in such a way as to admit an extended forward mobility of the attachment element (23) and of the back base element (11) during compression of the resilient stop device (29), whereby flexing of the knee joint is admitted in a loaded locked position.

12 Claims, 8 Drawing Sheets

DEVICE AT A KNEE JOINT PROSTHESIS

TECHNICAL FIELD

The present invention relates to a device at a knee joint prosthesis of the kind that comprises a polycentric link mechanism in accordance with the preamble of patent claim 1, as well as to an artificial knee joint in accordance with the preamble of the claims 4 and 10.

BACKGROUND OF THE INVENTION

Knee joint prostheses may be divided into two main categories:
1) The knee joint prostheses which lock at heel strike;
2) The knee joint prostheses that do not lock at heel strike.

The latter type will not be described further.

The former type may be further divided into different types, which at heel strike and during normal walking on a planar surface functions as follows:
   a) Manual locking prior to walking. Completely mechanical lock that does not permit any bending or shock absorption. Manual locking shoulder or piston being manoeuvred with an actuating lever or wire. Very simple technique where the prosthesis wearer walks with a straight leg and unlocks the knee before sitting down.
   b) Automatic locking at heel strike. Completely mechanical lock, which cannot be bent at all, and do not show any shock absorbing capacity. The lock may for instance be in the form of a frictional lock, when is activated by the body weight.
   c) Automatic locking at heel strike. It is possible to bend 10–15° with resistance and shock absorption, however it is not resilient, for instance hydraulics.
   d) Automatic lock at heel strike. It is possible to bend 10–15° with shock absorption and resistance from an elastic element, which springs back to an extended position.

The walking pattern of a person having an amputated thighbone considerably differs from normal walking due to the absence of important muscle groups. By means of the loss of the musculature of the knee, the person can no longer bend and then actively stretch the knee joint during load. It has earlier been attempted with assistance of different braking mechanisms, with more or less reliability, to prevent the leg from collapsing during the supporting phase, i.e., the time period that the foot is in contact with the supporting surface. Thus, different degrees of stability have been obtained. The amputated person puts down the prosthetic leg with a straight knee, which then remains straight during the major part of the support phase. If the mechanism of the knee joint is very stable, it is not possible to bend the knee until the support phase is completed. The absence of knee flexions in the beginning and end of the support phase makes the walk of a person with an amputated thighbone more energy demanding. The absence of calf musculature also leads to prosthetic walking that is more energy demanding than ordinary walking.

Knee joint prostheses having polycentric link mechanisms are previously known, such term relates to the fact that the center of rotation has different positions at different angels of the knee joint, i.e., there are multiple joint centers. The human knee joint is also polycentric. An example of a polycentric knee joint is shown in U.S. Pat. No. 2,638,605, where the locking of the knee joint at a straight knee is accomplished by a catch, that is released by a link mechanism, which transfers the movement of the toe region to the knee joint. However, this constructional solution is very complicated, and thereby suffers from the great disadvantage of making the knee joint heavy. Furthermore, it does not provide any natural finishing of the walking phase.

In WO 91/15170 a knee joint prosthesis is described, which is constructed in such a way as to resemble the function of the human knee joint, which in turn results in a more natural walk of the amputated person. The knee joint comprises a four-jointed polycentric link mechanism, in which the thigh bone prosthesis and the shank prosthesis are coupled by means of two links, one front and one back link, both jointed at either end to the thigh bone prosthesis as well as the shank prosthesis. The base link is of different length and attached to the shank prosthesis at different heights. The jointed attachment points of the shank prosthesis are arranged in mobile attachment elements, which, at a substantially straight knee joint, contribute so that the knee joint is in a substantially locked or mobile position, depending on the direction of the load on the knee joint. A mechanical lock stop, which may eventually be made from an elastically compliant material, is arranged to limit the forward movement of the back base link and its attachment elements as the knee joint is in a substantially straight position. This leads to the fact that the knee joint always is locked as long as the weight rests on the heel, and it cannot be unlocked even if considerable forces are applied to bend the joint. However, with assistance from the elastically compliant material in the mechanical lock stop the knee joint can be bent about 10–15° in a locked position with rebound. This resembles a normal walk and compensates the absence of the calf muscle during an ordinary walking. This cushioned slight outward flexing during normal walking is normally called stance flex. Thus, with stance flex in the following is intended an angle between the thigh bone-device and the shank device, which usually amounts to between 5° and 15°.

PURPOSE AND MAIN CHARACTERISTICS OF THE INVENTION

A first object with the invention is to provide a knee joint, which admits the possibility to a controlled bending of the knee to an angle exceeding the stance flex at load on the heel by means of that the moment of flexure is taken up by a resiliency device at the same time as springs back from this resiliency device is avoided at the swing phase of the leg. This object is achieved according to the invention by means of artificial knee joints in accordance with the characterizing part of claims 4 and 10.

A further object with the invention is to provide a knee joint that admits a controlled flexing of the knee up to an angle exceeding 20°, preferably at least 90° at load on the heel, by means of that moments of flexure are taken up by a resilient device, at the same time as spring from this resilient device is avoided during the swing phase of the leg. This object is also achieved, in accordance with the invention by means of artificial knee joints according to the characterizing part of claims 4 and 10.

A further object with the present invention is to achieve a farther development of the knee joint prosthesis mentioned above, where the stop function has been modified in such a way that it is possible to flex the knee joint at a higher degree with rebounding resistance as the load is on the heel, which is desirable, for instance, at walking in stairs and on inclined surfaces, as well as during practicing of certain sports, in order to obtain a natural pattern of walking and ability to move. This has been solved, according to the invention by means of the fact that the element of attachment shows a curved edge or similar, arranged to cooperate with the resilient stop device in such a way as to admit an increased mobility forward of the attachment element, and the back base element during compression of said resilient stop device, whereby flexing of the knee joint is admitted under load in a locked position.

The objective of the new modified stop function is to as large extent as possible to compensate for the lack of a working extensor musculature.

According to one embodiment, the curved edge or similar of the attachment device is arranged to act upon the resilient stop device via a dampening device. This may be constituted of a hydraulic system with an adjustable flow resistance. Hereby, the resistance at bending and active movement towards extension of the knee joint in a locked position may be adjusted for an individual adjustment. Hydraulic resistance, as well as spring back, may be individually adjusted.

DESCRIPTION OF THE DRAWINGS

In the following, the invention will be described in greater detail with reference to an embodiment shown on the accompanying drawings.

DESCRIPTION OF AN EMBODIMENT

The knee joint prosthesis shown in the figures consists of a polycentric link mechanism having a front 10 and a back base link 11, and an upper 12 and a lower connecting element 13, which are interconnected via seven fulcra 14–20. The upper connecting element 12 is connected to, and forms an integrated device with, a thighbone prosthesis 21, while the lower connecting element 13 is connected to and forms an integral part of a shank prosthesis 22. Further, the link mechanism is a part of a first and a second attachment element 23 and 24, which connect the shank prosthesis 22 to the front and the back base links 10 and 11, respectively. The shank prosthesis further carries an artificial foot 25.

The front and the back base link 10 and 11, are both joined at one end to the connecting element 12 attached to the thighbone prosthesis 21, and at a second end to the connecting element 13 attached to the shank prosthesis 22. The upper connecting element 12 has two attachment points 14, 15 for the front and the back base link 10 and 11, respectively. The lower connecting element 13 forms a substantially vertical upper extension of the shank prosthesis 22, and has in its lower end an attachment point 16 for the first attachment element 23, and in its upper end an attachment point 17 for the second attachment element 24.

The first attachment element 23, which is arranged at the lower part of the lower connecting element 13, may be compared to a tilt device having two attachment points, of which the first attachment point 16 constitutes an attachment point for the lower connecting element 13, and the second attachment point 18 constitutes a lower attachment point for the back base link 11.

The second attachment element 24, which is arranged at the upper end of the lower connecting element 13, shows a substantially triangular shape with three attachment points, whereby the attachment point 17 being located between the other two 19, 20, constitutes the attachment point for the lower connecting element 13. The two other attachment points 19 and 20 constitute attachment points for the front 10 and the bad 11 base links, respectively. The second attachment element 24 works as a balance scale that moves depending on the movement of the body's center of gravity. The attachment point 17 to the lower connecting link 13 is the point around which the second attachment element 24 is mobile.

The first attachment element 23 shows a curved edge or cam curve 26 which is arranged to cooperate with a cam follower, such as a roller 27 contacting a hydraulic piston 28 arranged in the shank prosthesis 22, which in turn contacts an elastic element 29 functioning as a resilient stop device, for instance a rubber element.

Figure 1:
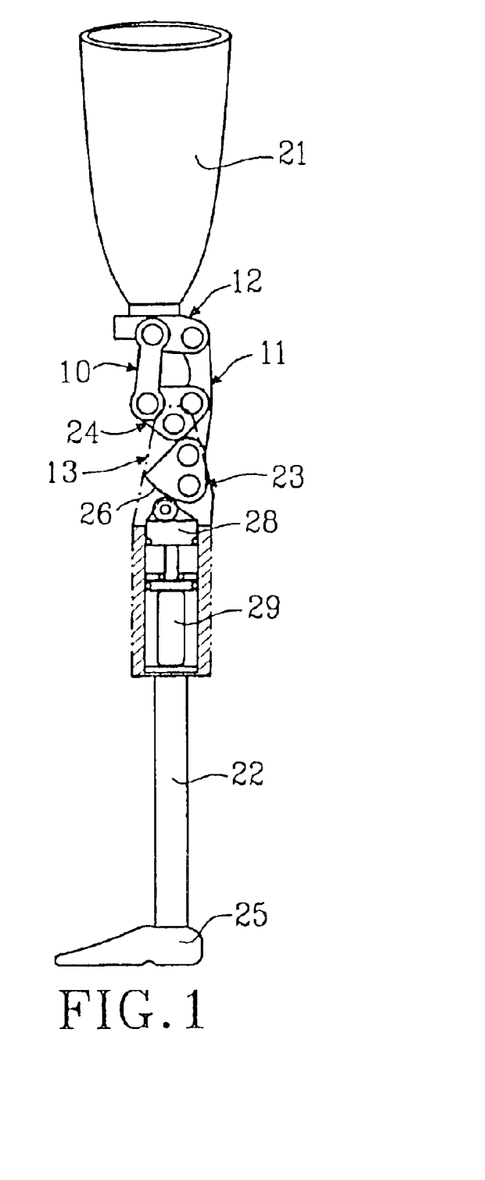
FIG. 1 schematically shows leg prosthesis in upright position according to the invention.
Figure 2:
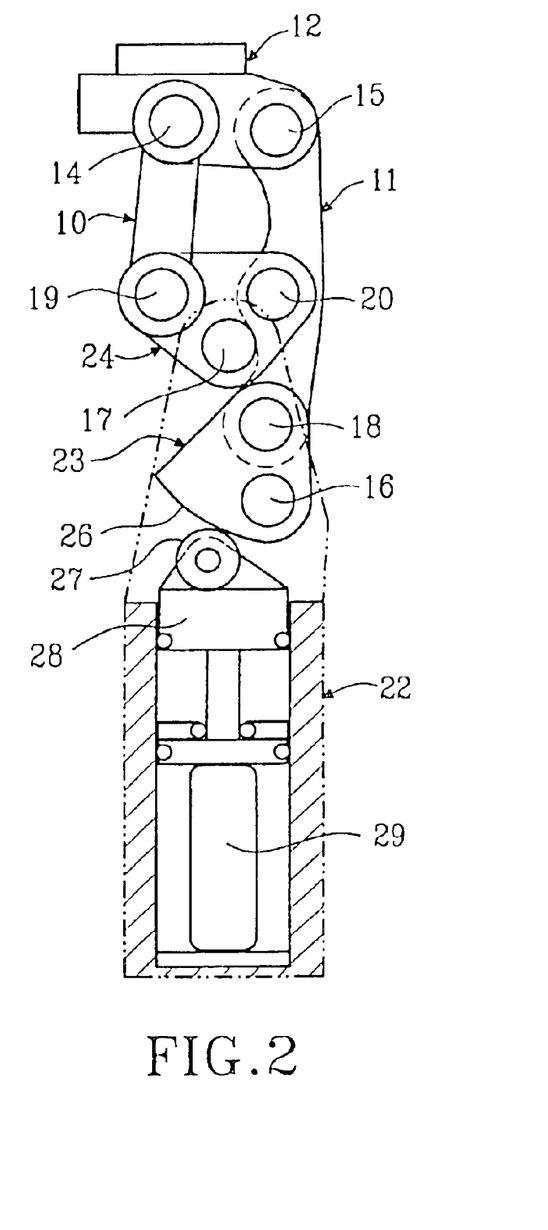
FIG. 2 shows the knee joint prosthesis according to FIG. 1 on a larger scale.

The knee joint prosthesis works in the following way. With the knee joint in a substantially extended position and with the load on the heel, i.e., the position shown in FIGS. 1 and 2, the second attachment element 24 will move clockwise around the attachment point 17, and force the first attachment element 23 to contact the roller 27. Since further movement forward of the first attachment element 23 is prevented when its curved edge or cam curve 26 comes into contact with a cam follower such as the roller 27, a locking of the knee joint occurs so that it does not bend during normal load on the knee joint, as is exerted in a standing still position.

Figure 3:
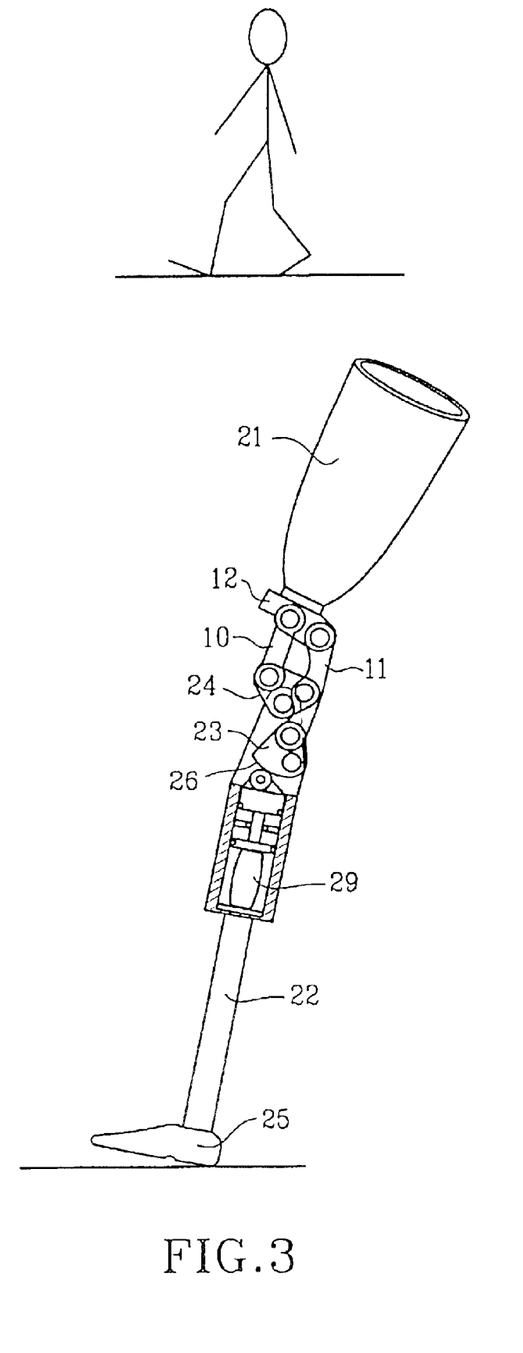
FIG. 3 schematically shows the leg prosthesis having a knee joint prosthesis according to the invention in a loaded, somewhat bent position related to ordinary walking.
Figure 4:
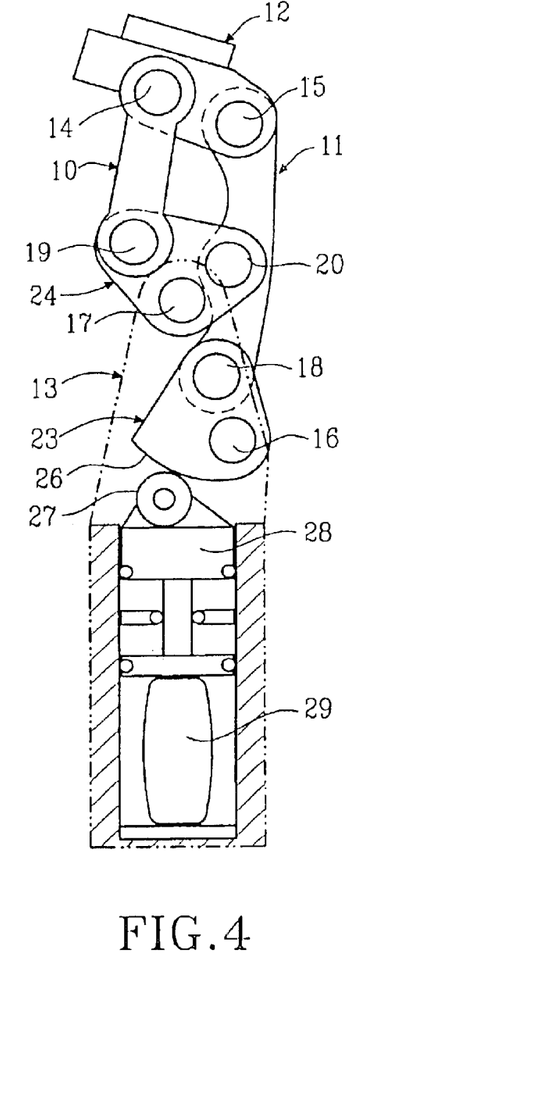
FIG. 4 shows the knee joint prosthesis, according to FIG. 3 on at a larger scale.

In FIGS. 3 and 4 the position for heel strike in relation to normal walking, is shown. The additional load, which is hereby subjected to the knee joint, compared to a standing still position, is sufficient to force the curved edge to rotate counter-clockwise around the attachment point 16, and thereby press the roller 27 and the hydraulic piston 28 downwards against the action of the rubber element 29. Thereby resilience is admitted at putting down the heel in relation to walking, with accompanying locking, in such a way as showing great similarities to the human gait.

Figure 5:
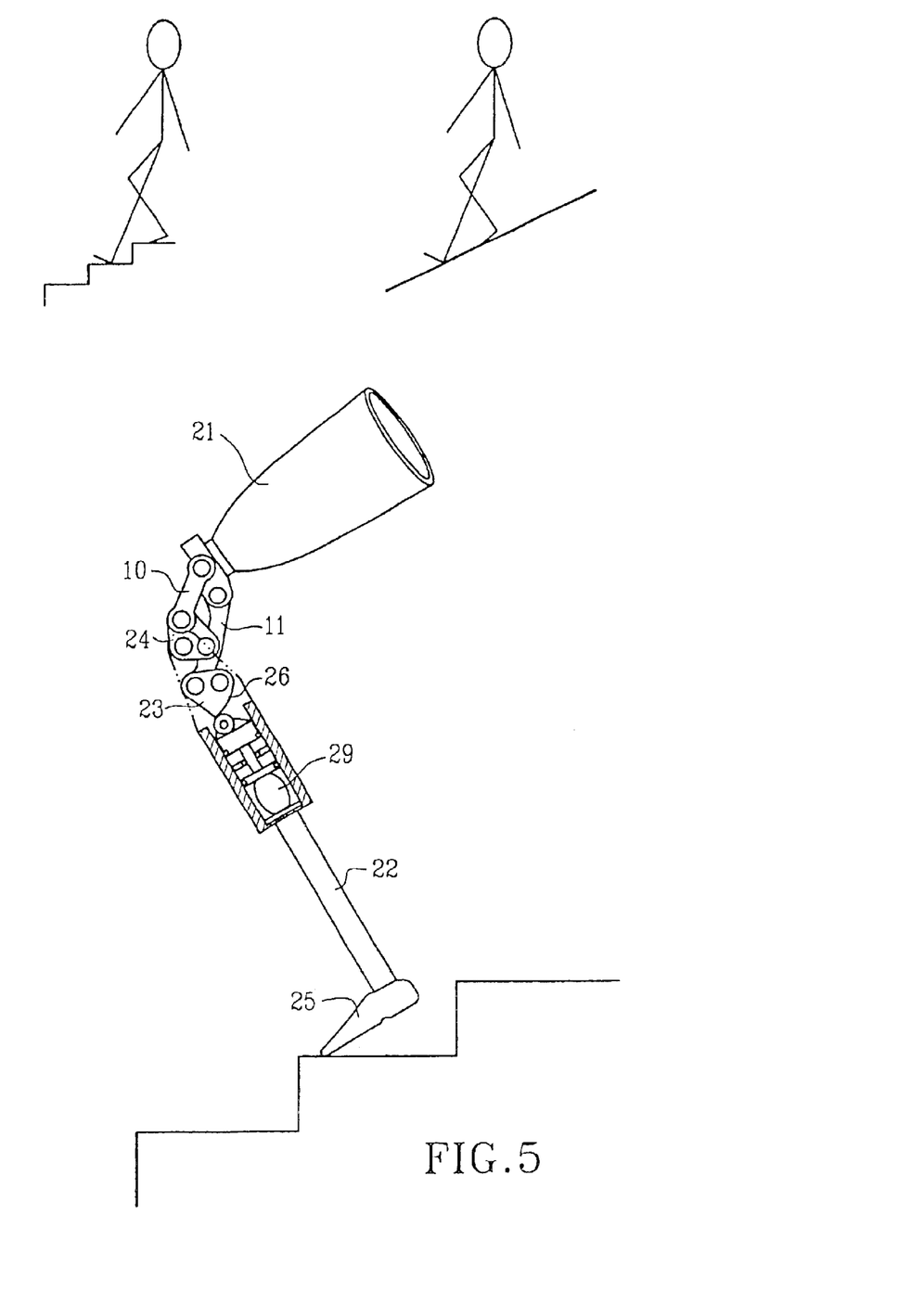
FIG. 5 schematically shows the leg prosthesis having the knee joint prosthesis, according to the invention, in a loaded, somewhat bent position at heel strike related to walking down stairs.
Figure 6:
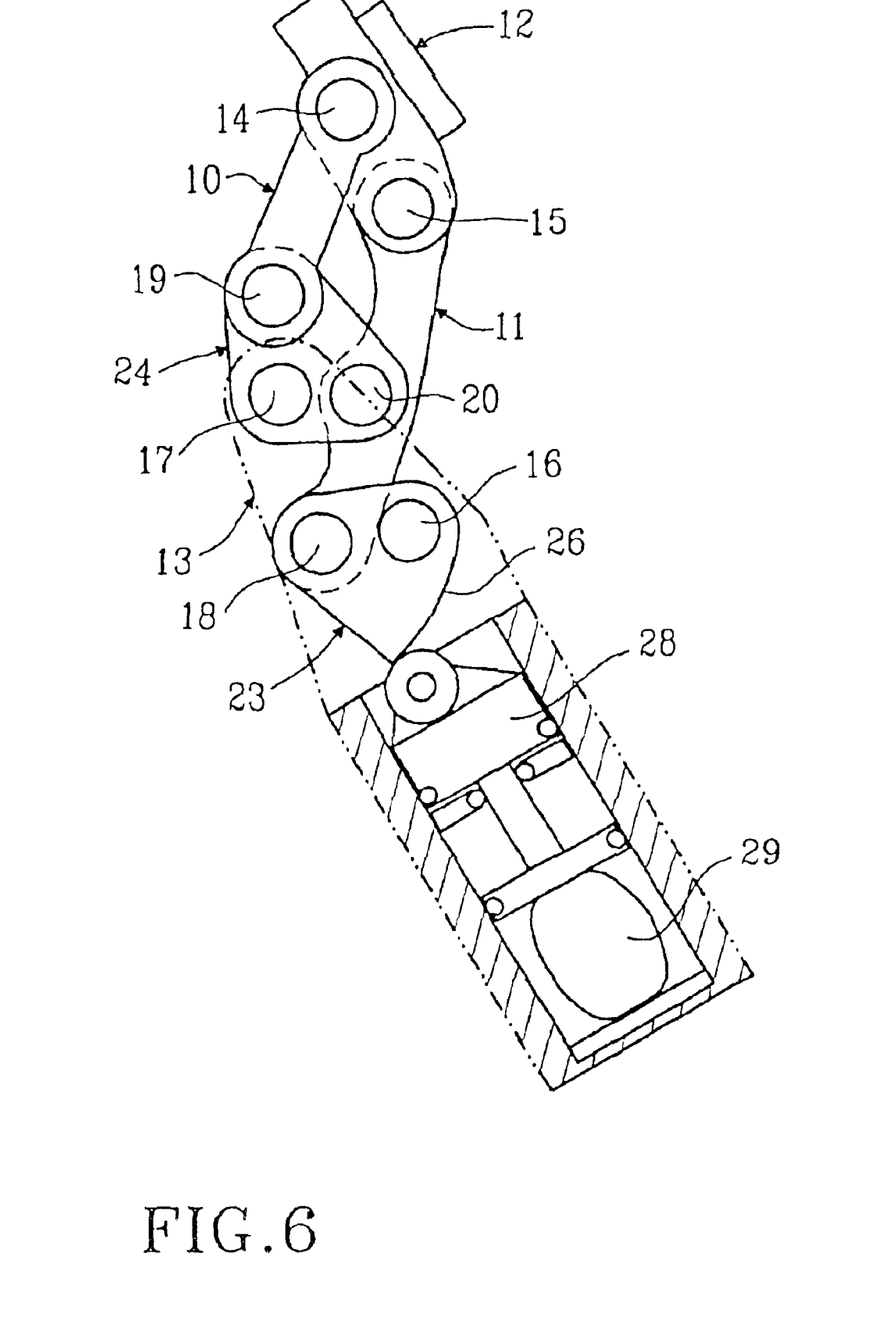
FIG. 6 shows the knee joint prosthesis according to FIG. 5 on a larger scale.

In FIGS. 5 and 6 a position is shown when walking down stairs, when it is desirable to be able to bend the knee to an even higher extent than in the position shown in FIGS. 3 and 4, when the body weight is on the heel. The curved edge or cam curve 26 has now been forced to rotate a further distance counter-clockwise around the attachment point 16, thereby forcing the cam follower (e.g., roller) 27 and the hydraulic piston 28 downwards during simultaneous compression of the rubber element 29. In the position shown the knee joint has been bent approximately 90° under load, which in the example shown is the maximum response and which should be sufficient for most activities, including practicing sports. With the new knee joint, a very natural pattern of ability to move is enabled, for instance when walking up and down stairs. The heel is put down on the stair, and with the body weight on the heel the knee joint may be bent up to 90°, in a controlled and smooth manner, against the action of the resilient rubber element 29.

Figure 7:
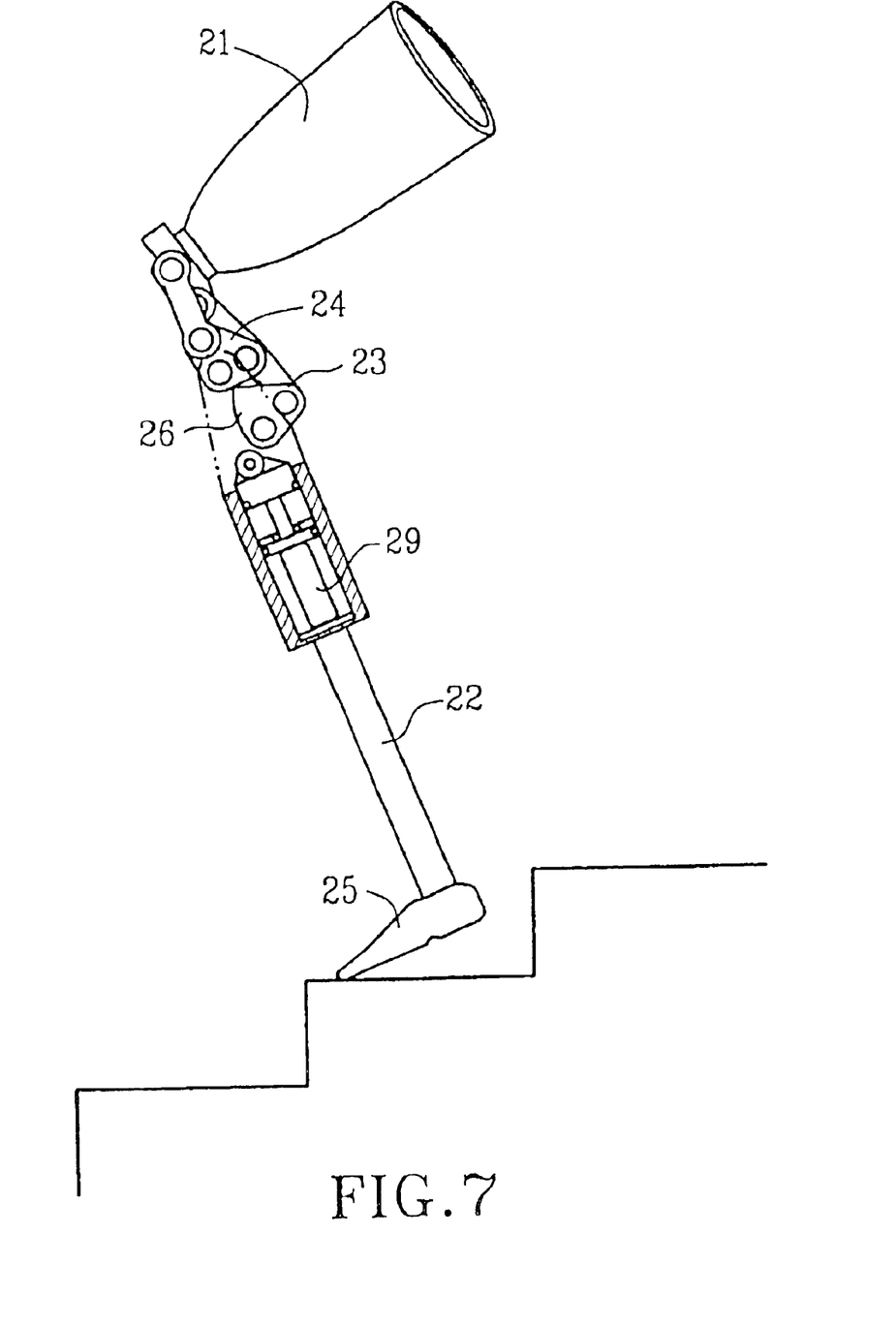
FIG. 7 schematically shows the leg prosthesis having the knee joint prosthesis, according to the invention in a loaded position with the load on the toe.

An alternative way of bending the knee joint when, for example, climbing stairs, is shown in FIG. 7, This way, along with the knee joint described in WO 91/15170, was previously the only way to bend the knee joint in a position under loads i.e., to put down the entire foot and roll over on the toe, thereby locking the knee joint stops by means of the second attachment element 24 having been forced over in the counter-clockwise direction, thereby forcing the link system to move so that the first attachment element 23 has swung away from the lock position, thus allowing the knee joint to be freely bent. However, this implies an uncontrolled bending and not, as per above, a controlled, smooth bending.

Figure 8:
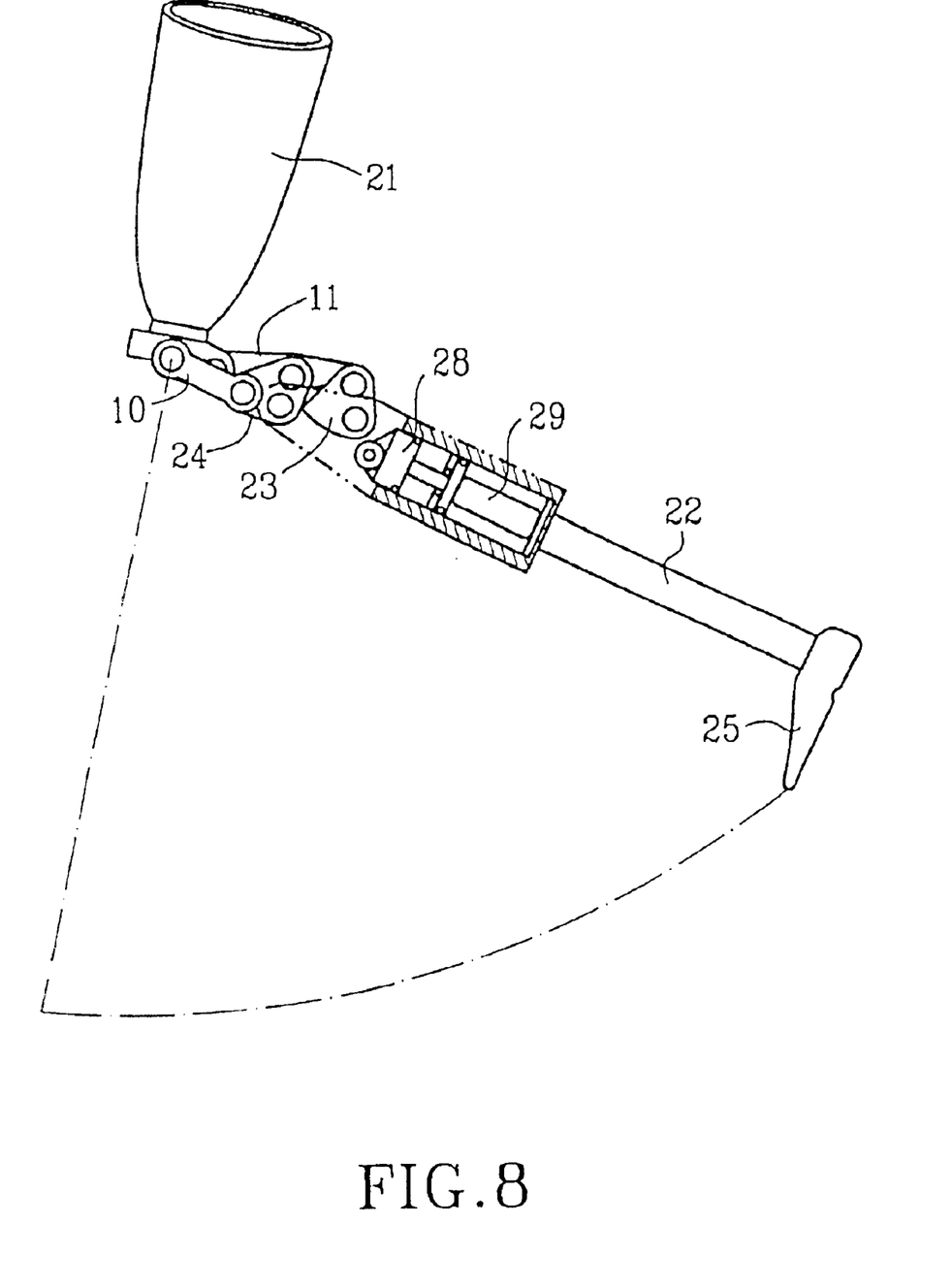
FIG. 8 schematically shows the leg prosthesis with the knee joint prosthesis, according to the invention in an unloaded position having a free swing backwards.
Figure 9:
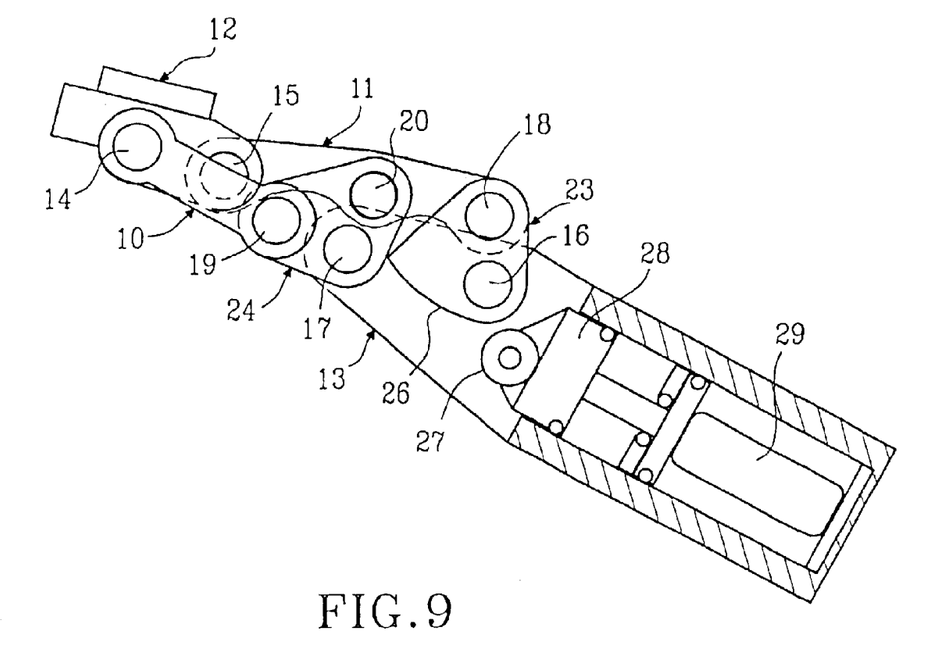
FIG. 9 shows the knee joint prosthesis according to FIG. 8 on a larger scale.

In FIGS. 8 and 9 an unloaded position is shown, in which the knee joint may be flexed in such a way that the shank prosthesis can be swung freely backwards. This naturally occurs at the settlement of the step during walking. Thus, the lock function does not prevent the settlement of the step. In this position the first attachment element 23 has been bent backward, which is the consequence of a load on the front part of the foot, 25. This leads to that the curved edge 26, located at the first attachment element 23, being disengaged from its cooperation with the rubber element 29, whereby the shank part and the thighbone part may be flexed with respect to each other without any influence from the rubber element 29. At walking this situation is obtained at the settlement of the step. This phase after the settlement of the step is denominated called the swing phase, and constitutes the phase in which the leg should take back its prolonged position prior to a new impact. If resilience occurred against the rubber element 29, which is adapted to be able to spring, preferably up to a 90° angle between the shank device and the thighbone device, spring back would occur with a violent force after a large flex. During the swing phase the prosthesis may of course be provided with further means for separate control of the movement of the swing phase. These means preferably comprise resilient devices as well as dampening devices.

Figure 10:
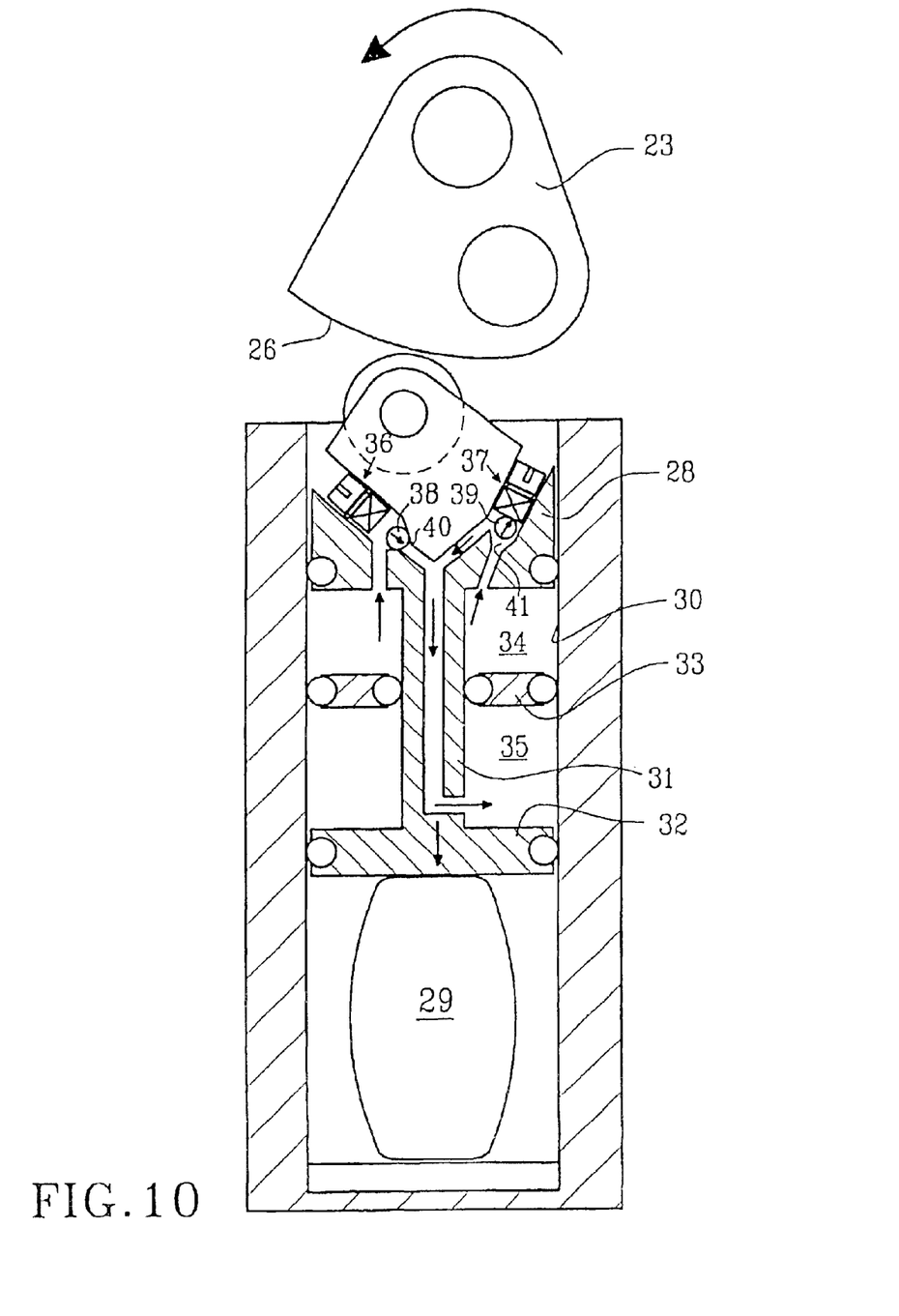
FIG. 10 schematically shows the hydraulic mechanism, which transfers the movement of the cam curve to the resilient stop device.

FIG. 10 shows the hydraulic mechanism that transfers the pressure from the curved edge 26 to the roller 27 to the rubber element 29. It comprises a hydraulic cylinder 30, filled with hydraulic fluid, a hydraulic piston 28 with a hollow piston rod 31 connected thereto, which is finished in a supporting plate 32 contacting the rubber element 29. In the hydraulic cylinder 30 is further arranged a dividing wall 33, which is sealed against the piston rod 31 and divides the hydraulic cylinder into an upper and a lower chamber 34 and 35, respectively. They hydraulic piston 28 shows flow passages for the hydraulic fluid, in which passages a pair of non-return valves 36, 37, having a valve ball 38, 39 each are arranged which may seal against one corresponding valve seat 40, 41.

As the knee joint is to be bent in a loaded position the curved edge or cam curve 26 rotates around the attachment point 16 and presses the cam follower (e.g., roller) 27 downwards. This, in turn, pushes the hydraulic piston 28 downward in the cylinder 30 and hydraulic fluid is forced from the upper chamber 34 to the lower chamber 35. The non-return valve 36 is hereby closed by means of the valve ball 38 being pressed against its valve seat 40, while the second non-return valve 37 is opened by means of the ball being pushed upwards, away from its valve seat 41. After that the hydraulic fluid passes through the hollow piston rod 31 down into the lower chamber 35. Thus, the pressure from the roller 27 and the hydraulic piston 28 is transferred to the rubber element 29 via the described hydraulic mechanism, which achieves a smooth dampening of the movement. In a simplified variant the hydraulic mechanism may be excluded and the pressure of the cam curve 26 and the roller 27 is directly transferred onto the rubber element 29.

As the load on the knee joint stops, the compressed rubber element 29 pushes against the supporting plate 32 of the piston rod 31, and the knee joint is pressed back into an extended position via the hydraulic piston 28, the roller 27, and the curved edge 26. The movement is dampened by means of that hydraulic fluid in relation hereto is pressed from the lower chamber 35 into the upper chamber 34 via the non-return valve 36, while the non-return valve 37 is closed.

Thus, the purpose of the hydraulic mechanism is to slow down the movement of the resilient element during compression and expansion, whereby a user is offered the possibility to control the prosthesis using less force. The hydraulic mechanism is adopted to the activity level and body weight of the user, as well as to the characteristics of the resilient element, such as, for instance, e-modulus.

The new knee joint may bend up to 90° having high resistance. It is capable of actively springing back, and can carry the body weight from a flexed to a straight leg on the spring back force. It is therefore possible to perform knee-bends and actively push-up to an upright position of the prosthetic leg. Thus, the prosthesis carrier acquires the ability to actively compensate the front lost thigh muscle in certain situations.

The great advantage of the new knee joint prosthesis is, above all, in walking on stairs and hills. It provides an improved possibility for controlling the walk, and to walk slowly and naturally down stairs and hills, a function that has been absent in previously known knee joint prosthesis. In a locked position, the new knee joint can be flexed up to 90°, and it can further be lifted up and brought forward in this position. The rubber element 29 pushes upwards and forces the knee joint into an extended position. The hydraulics regulate the swing back to an extended position, in such a way that the force the rubber element exerts does not result in an uncontrolled swing. The hydraulics, which are in effect at both a locked bend and during re-swing swing to the extended position, may be adjusted to comply with the desires and needs of the patient. The non-return valves 36 and 37, and thus the flow rate of hydraulic fluid, may be adjusted differently in the two directions.

During skiing the new knee joint may provide the possibility to flex up and down with bent knees in a controlled manner. It is possible to regain a large part of the muscle control that one has when flexing the knee with a healthy leg. When practising sports such as, for instance, basketball it is important to be able to perform quick stops and turns, which the new knee joint enables. It is thus possible to regain an enhanced mobility and control in the daily life.

For a detailed description of the basic components of the artificial link mechanism refer to WO91/15170, which description is incorporated into this specification. This document, however, does not describe a first attachment element, which is arranged to admit great flexing of the knee during rebound, whereby the person carrying the prosthesis is compensated for the missing stretch musculature.

The invention is not limited to the embodiment shown in the drawings and described above, but may be varied within the scope of the patent claims. Thus, the invention may be applied in other types of polycentric knee joints than the knee joint shown.

What is claimed is:

1. An artificial knee joint with a pair of link mechanisms, the artificial knee joint comprised of:
   a thighbone prosthesis (21) and a shank prosthesis (22) connected by a front and a back base link (10,11), both base links (10,11) having a first end, where the first end of the back base link (11) is joined to a first attachment element (23) and the first end of the front base link (10) is joined to a second attachment element (24), with each attachment element (23,24) being attached to attachment points (16,17), respectively, on the shank prosthesis (22); and both links (10,11) having a second end attached to an upper connecting element (12) connected to the thighbone prosthesis (21), whereby the attachment points (16,17) of the shank prosthesis (22) are arranged in the movable first and second attachment elements (23,24) so that at a substantially straight knee, the link mechanisms (10,11) is located at a first position, and a second position, when the knee is bent, where the knee joint further comprises a resilient stop device (29), characterized by:

the first attachment element (23) cooperating, through a cam follower (27), with said resilient stop device (29) to admit flexing of the thighbone prosthesis (21) in relation to the shank prosthesis (22) up to an angle exceeding stance flex during compression of said stop device (29) at said first position; and disengaging from said resilient stop device (29) at said second position.

2. The artificial knee joint according to claim 1, characterized by: at least one of said attachment elements positioned to cooperate with said resilient stop device to admit flexing of the thighbone prosthesis in relation to the shank prosthesis during compression of said stop device up to an angle exceeding 20°, preferably at least 90° at the said first position.

3. The artificial knee joint according to claim 1, characterized by: the link mechanisms of the knee joint positioned to allow said first position at load on the heel and said second position at load on the toe whereby a swing phase present during walking is allowed without spring back of the shank portion from said resilient stop device.

4. The artificial knee joint according to claim 1, in which the back base link is pivotably attached at its upper end to an upper connecting element and pivotably connected at its lower end to a lower connecting element through said first jointed attachment element, characterized by: said first attachment element positioned to cooperate with said resilient stop device to admit flexing of the thigh part with respect to the shank part to an angle exceeding 20°, preferably at least 90° during compression of said stop device.

5. The artificial knee joint according to claim 4, characterized by: said attachment element having a cam curved positioned to cooperate with said resilient stop device.

6. The artificial knee joint according to claim 5, characterized by: said cam curve contacting a cam follower that is positioned to transfer pressure force from the cam curve to the resilient stop device via a hydraulic mechanism.

7. An artificial knee joint comprised of:

an upper connecting element (12) capable of mating with a thighbone prosthesis (21), the upper connecting element (12) having a front attachment point (14) and a back attachment point (15), a lower connecting element (13) having an upper end and a lower end with an upper attachment point (17) at the upper end and a lower attachment point (18) displaced toward the lower end at a distance below the upper attachment point (17), whereby the lower end of the lower connecting element (13) constitutes a part of a shank prosthesis (22);

a front base link (10) having opposite ends with attachment points (14,19) at each end whereby one end is pivotally connected to the front attachment point (14) of the upper connecting element (12);

a back base link (11) having opposite ends with attachment points (15,18) at each end and at least one attachment point (20) there between whereby one end of the back base link is pivotally connected to the back attachment point (15) of the upper connecting element (12);

a first attachment element (23) comprising a link with at least two attachment points (18,16), whereby one attachment point (16) is pivotally connected to the lower attachment point (16) of the lower connecting element (13) and the other attachment point (18) is pivotally joined to the lower attachment point (18) of the back base link (11);

a second attachment element (24) comprising a link having at least three attachment points (17,19,20), whereby the third attachment point (17) is united with the upper attachment point (17) of the lower connecting element (13) and the first and second attachment points (19,20) are movably connected to the lower attachment point (19) of the front base link (10) and the middle attachment point (20) of the back base link (11), respectively; and a resilient stop device (29), the artificial knee joint characterized by:

the first attachment element (23) positioned to cooperate, through a cam follower (27), with said resilient stop device (29) for admitting flexing of the thighbone prosthesis (21) in relation to the shank prosthesis (22) up to an angle exceeding stance flex during compression of said stop device (29) at a first position and that said first attachment element (23) is arranged to be disengaged from said resilient stop device (29) at a second position.

8. The artificial knee joint according to claim 7, characterized by: at least one of said attachment elements positioned to cooperate with said resilient stop device to admit flexing of the thighbone portion with respect to the shank portion during compression of said stop device up to an angle exceeding 20°, preferably at least 90° at the said first position.

9. The artificial knee joint according to claim 7, characterized by: the link mechanisms included in the knee joint positioned to assume said first position when load is on the heel and said second position when load is on the toe whereby a swing phase present during walking is admitted without spring back from said resilient stop device.

10. The artificial knee joint according to claim 9, characterized by: said first attachment element exhibits a cam curve arranged to cooperate with said resilient stop device.

11. The artificial knee joint according to claim 10, characterized by: said cam curve contacting a cam follower which is arranged to transfer pressure force from the cam curve to the resilient stop device via a hydraulic mechanism.

12. The artificial knee joint according to claim 11, characterized by: different parts of the artificial joint being dimensioned and arranged in such a way that the cam curve is pushed harder against the resilient stop device at an increasing load when the body weight rests against the heel while the cam curve leaves the contact against the cam follower as the weight is transferred to the toe whereby a swing phase present when walking is admitted without spring back from said resilient stop device.

* * * * *